US012788562B2

(12) United States Patent
De Bonis et al.

(10) Patent No.: US 12,788,562 B2
(45) Date of Patent: Nov. 10, 2026

(54) ARTICULATED PROSTHESIS FOR A TRICUSPID OR MITRAL VALVE AND RELATED CATCHING DEVICE

(71) Applicant: STAR TRIC S.R.L., Milan (IT)

(72) Inventors: Michele De Bonis, Cernusco Sul Naviglio (IT); Ottavio Alfieri, Brescia (IT); Elisabetta Lapenna, Cernusco Sul Naviglio (IT); Daniele Zanotti, Comelico Superiore (IT); Marco Gard, Borgomasino (IT); Eugenio Maria Passanante, Milan (IT)

(73) Assignee: STAR TRIC S.R.L., Milan (IT)

( * ) Notice: Subject to any disclaimer, the term of this patent is extended or adjusted under 35 U.S.C. 154(b) by 389 days.

(21) Appl. No.: 18/703,887

(22) PCT Filed: Nov. 10, 2021

(86) PCT No.: PCT/IB2021/060386
§ 371 (c)(1),
(2) Date: Apr. 23, 2024

(87) PCT Pub. No.: WO2023/084270
PCT Pub. Date: May 19, 2023

(65) Prior Publication Data
US 2024/0415653 A1 Dec. 19, 2024

(51) Int. Cl.
*A61F 2/24* (2006.01)

(52) U.S. Cl.
CPC ............ *A61F 2/2463* (2013.01); *A61F 2/246* (2013.01); *A61F 2/2466* (2013.01); *A61F 2210/0009* (2013.01); *A61F 2210/0014* (2013.01); *A61F 2220/0016* (2013.01)

(58) Field of Classification Search
CPC ...... A61F 2/246; A61F 2/2463; A61F 2/2466; A61F 2220/0016; A61F 2220/0025; A61F 2220/0075; A61F 2230/0013; A61F 2/2454; A61F 2220/0008; A61F 2220/0091; A61B 17/0057; A61B 17/08; A61B 17/083
See application file for complete search history.

(56) References Cited

U.S. PATENT DOCUMENTS

| | | | | |
|---|---|---|---|---|
| 10,123,873 | B1 | 11/2018 | Metchik et al. | |
| 2016/0174979 | A1* | 6/2016 | Wei .................... | A61B 17/1285 606/151 |
| 2018/0325661 | A1* | 11/2018 | Delgado ................. | A61F 2/246 |
| 2019/0000613 | A1 | 1/2019 | Delgado et al. | |
| 2019/0365529 | A1 | 12/2019 | Siegel et al. | |
| 2024/0008983 | A1* | 1/2024 | Zhang ..................... | A61F 2/246 |

OTHER PUBLICATIONS

International Search Report and Written Opinion for Corresponding International Application No. PCT/IB2021/060386, Jul. 27, 2022, 10 pages.

* cited by examiner

*Primary Examiner* — Sarah W Aleman
*Assistant Examiner* — Paris Marie Blass
(74) *Attorney, Agent, or Firm* — LUCAS & MERCANTI, LLP

(57) ABSTRACT

A prosthesis, left in the patient's heart to repair the tricuspid or mitral valve, is made to simultaneously hold all three tricuspid valve flaps, or the two mitral valve flaps, to keep them fully extended in the plane of the valve and to assume a final configuration as in the common surgical procedure. A device for repairing a tricuspid or mitral valve including such a prosthesis is also disclosed.

11 Claims, 23 Drawing Sheets

ARTICULATED PROSTHESIS FOR A TRICUSPID OR MITRAL VALVE AND RELATED CATCHING DEVICE

CROSS-REFERENCE TO RELATED APPLICATIONS

This application is a 371 of PCT/IB2021/060386, filed Nov. 10, 2021.

Field of the Invention

This disclosure relates to the repair of heart valves showing regurgitation. More particularly, the invention relates to an apparatus suitable for a less invasive repair of a heart valve using an articulated prosthesis of a catching device, which can be positioned through a catheter, for the flaps of a tricuspid or mitral valve.

BACKGROUND OF THE INVENTION

The most common type of tricuspid valve dysfunction is functional tricuspid regurgitation (TR), which is mainly due to dilation of the tricuspid annulus after the dilation of the right ventricle. Later in the course of the disease, a "tethering" of the tricuspid flaps may also take place due to the dislocation of the papillary muscles within the remodeled right ventricle. When functional TR is due to both severe annular dilation and flap chaining, annuloplasty alone is unlikely to be effective. Similarly, TR caused by prolapse or "flail" of multiple flaps, as typically seen in post-traumatic TR and severe degenerative TR, cannot be corrected by a simple annuloplasty procedure.

In order to obtain an effective and lasting repair, the so-called "clover" technique has been proposed. This technique consists of tying together the central part of the free edges of the tricuspid flaps, producing a valve in the shape of a "clover". A visual representation of a tricuspid valve treated according to this technique is shown in FIG.

1. Clinical Results Obtained with this Technique are Reported in:

- "*The 'clover technique' as a novel approach for correction of post-traumatic tricuspid regurgitation*". O. Alfieri, M. De Bonis et al., Journal of Thoracic and Cardiovascular Surgery, 2003; Vol. 126, No. 1, pages 75-79;
- "*A novel technique for correction of severe tricuspid valve regurgitation due to complex lesions*." De Bonis M. Lapenna E et al. Eur. J. Cardiothorac. Surg. 2004 May; 25 (5): 760-5.
- "*Four-leaflet clover repair of severe tricuspid valve regurgitation due to complex lesions*", E. Lapenna. M. De Bonis et al., Journal of Cardiovascular Medicine. 2008, Vo. 9 No. 8, pages 847-849;
- "*The clover technique for the treatment of complex tricuspid valve insufficiency: midterm clinical and echocardiographic results in 66 patients*". E. Lapenna, M. De Bonis et al., European Journal of Cardio-thoracic Surgery, 37 (2010), 1297-1303;
- "*Long-term results (up to 14 years) of the clover technique for the treatment of complex tricuspid valve regurgitation*", De Bonis M. Lapenna E, et al. Eur. J. Cardiothorac. Surg. 2017 Feb. 23. doi: 10.1093/ejcts/ezx027.

Devices for catching opposite flaps of a mitral valve as well as a tricuspid valve are sold under the trade names MITRACLIP™ and TRICLIP™. This prior device, which can be introduced into the heart through a catheter in a blood vessel or through a small incision in the chest, comprises an applicator of a catching device of the type shown in FIG. 2. The sequence of operations to be performed to implant a device MITRACLIP™ catching device is shown in FIG. 3. In the illustrated case the heart valve is the mitral valve, but the same observations apply mutatis mutandis also for the tricuspid valve. Using a catheter, the MITRACLIP™ catching device is inserted in a folded configuration into the heart; when the catheter is close to the heart valve, the latch is deployed like an umbrella to catch the valve flaps, and is subsequently closed to hold the flaps together. Finally, the MITRACLIP™ catching device is left closed in the heart to hold the flaps together, thereby reducing valve regurgitation.

SUMMARY

Unfortunately, tests performed by the Applicant have shown that this known applicator with two arms is unable to simultaneously catch all three flaps of the tricuspid valve, thus its effectiveness in treating tricuspid regurgitation is very limited. In the presence of a very dilated tricuspid annulus, even catching only two flaps of the tricuspid valve is quite difficult with the MITRACLIP™ device. When more MITRACLIP™ devices are implanted in order to improve the continence of the tricuspid valve, the risk of tricuspid stenosis increases significantly, greatly reducing the area of the repaired tricuspid valve. In order to prevent this problem, the device of the present disclosure is designed to simultaneously retain all three flaps of the tricuspid valve, or the two flaps of the mitral valve, so as to maintain them assuming a final configuration as in the common surgical procedure.

This exceptional result is achieved with a prosthesis as defined in the appended claim 1. The prosthesis is the portion, left in the patient's heart, of a related device for repairing a tricuspid or mitral valve, comprising a prosthesis of this disclosure inserted in a catheter for interventions.

Further embodiments are defined in the attached claims. The claims as filed are an integral part of the present description and are incorporated herein by express reference.

DETAILED DESCRIPTION OF EXAMPLE EMBODIMENTS

Figure 1:
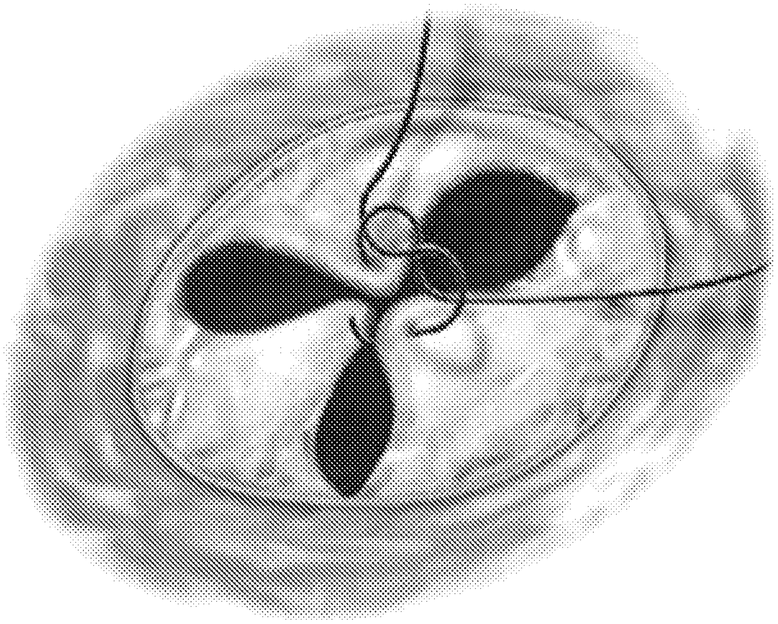
FIG. 1 schematically shows a typical configuration of a tricuspid valve after surgery with the so-called "clover" technique.
Figure 2:
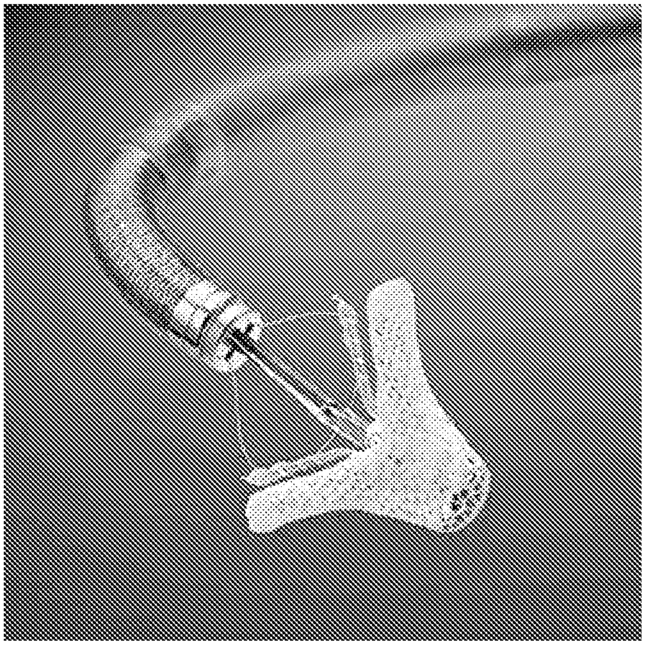
FIG. 2 shows a known attachment device for flaps of a tricuspid or mitral valve.

Prostheses of this disclosure for repairing a tricuspid or mitral valve are schematically illustrated in FIGS. 4 to 24.

In the follofin description reference will be made to the repair of a tricuspid valve, but the same observations apply mutatis mutandis to the repair of a mitral valve. For this reason, the prosthesis shown in the figures has angularly spaced triples of fins for catching the three flaps of a tricuspid valve. However, the prosthesis shown could be made with two pairs of fins or with two groups with more than three fins each for catching the flaps of any heart valve. Furthermore, it is not essential that the triplets of fins are arranged with radial symmetry, as exemplified in the figure: the fins may be angularly spaced one from the other in various ways to adapt to the anatomy of the patients' heart valves.

In one aspect, a prosthesis for a tricuspid or mitral valve of this disclosure comprises a first tubular support 1 having a first tubular body, terminating at its distal end with an cap 2 open like an umbrella. The cap 2 defines, together with the outer wall of the first tubular support 1, a cavity open on one side.

Optionally, the first tubular support 1 has a longitudinal axial hole through which to pass a guide wire, of the type commonly used in surgery to position heart valves to be implanted.

The prosthesis of this disclosure also has a second tubular support 3 having a second tubular body with a respective longitudinal axial hole, with a first plurality of fins 4 constrained to a distal portion of the second tubular support 3, and a third tubular support 5, having a third tubular body with a respective longitudinal axial hole, having at least a second plurality of fins 6 constrained to a distal portion of the third tubular support 5. The fins of the first plurality of fins 4 and of the second plurality of fins 6 are configured to pass autonomously from a respective retracted configuration, in which they are extended longitudinally along an external wall respectively of the second tubular support 3 and of the third tubular support 5, to a respective open configuration, in which they are open radially away from the external wall of the second tubular support 3 and of the third tubular support 5, respectively, as soon as they are free to unfold.

In the exemplary embodiment shown in FIGS. 4 to 14, each plurality of fins 4 and 6 is formed by three fins, because the prosthesis shown is made for tricuspid valves. Conveniently, the first plurality of fins 4 comprises three first fins angularly spaced by 120°, and the second plurality of fins 6 comprises three second fins angularly spaced by 120° placed in front of the first plurality.

As already mentioned, it is not essential that the fins are regularly spaced by 120°. It is possible to space the fins unevenly from each other to adapt to the anatomy of the patient's heart valve. Furthermore, it is not essential to have fins of the same shape and size, as shown in the attached drawings, but it will be possible for example to make a first plurality of fins 4 wider or longer than the second plurality of fins 6 or vice versa.

However, it is possible to make each plurality of fins with two or four or even more fins to better catch the flaps of the heart valves.

The second tubular support is configured to slide in a longitudinally guided manner over the outer wall of and concentrically to the body of the first tubular support 1, just as the third tubular support 5 is configured to slide in a longitudinally guided manner over the outer wall of and concentrically to the body of the second tubular support 3 and above the first plurality of fins 4 in a retracted configuration.

The fins of the first plurality of fins 4 and of the second plurality of fins 6 have respective facing surfaces 7 and 8 configured to cooperate with each other to catch a flap of a tricuspid or mitral valve by squeezing it like a jaw from opposite faces.

According to an optional aspect, the respective facing surfaces 7 and 8 of the fins of the first plurality of fins 4 and of the second plurality of fins 6, respectively, have teeth and/or harpoons 14 for catching the flaps of a tricuspid or mitral valve. In the example shown in the figures, the fins 4 have a knurling while the fins 6 have harpoons, but nothing prevents from having a different configuration from the one shown. For example, to have reversible catching mechanisms, fins 6 could be made which have harpoons or spikes which engage in corresponding concavities made on the fins 4. Alternatively, fins 4 and 6 could be made, both with a knurling or with a significant surface roughness whereby, by pressing the fins 4 and 6 so as to pinch a flap of a heart valve, this is firmly held by friction.

As shown in the succession of figures, the second tubular support 3 is pushed so as to free the fins 4 of the first plurality of fins. As soon as they are outside the third tubular support 5, they extend radially by themselves opening like "petals". In the embodiment shown in FIGS. 4 to 14, the third tubular support 7 is pushed so as to free the fins 6 of the second plurality of fins. Like the fins 4 of the first plurality, the fins 6 also extend radially by themselves.

The automatic opening of the fins 4 and 6 may be conveniently implemented by making the fins 4 and 6 in a shape memory material, such as Nitinol. Alternatively, the fins 4 and 6 could be made of elastic material so that as soon as they come out of the third tubular support 5, they tend to elastically open. In this way, the fins 4 and 6 will remain extended along the second tubular support 3 and the third tubular support 5 until the prosthesis is in the closed configuration of FIG. 4, in which it will be distributed, but they will open to catch the flaps of a valve heart as soon as they are free to move.

In order to catch the flaps of a valve, the second tubular support 3 and the third tubular support 5 are pushed so as to bring the fins 4 of the first plurality closer to the corresponding fins 6 of the second plurality and so as to insert the distal portion of the second tubular support 3, to which the fins 4 of the first plurality of fins are fixed, inside the cavity defined by the cap 2 with the first tubular support 1. By forcefully pushing the second 3 and third 5 tubular supports into the cavity, the fins 4 of the first plurality remain wedged between the edge of the cap 2 and the third tubular support 5, so that a flap of a heart valve sandwiched between the fins 4 and 6 will be firmly held in place.

In the embodiment illustrated in FIGS. 4 to 14, the outer wall of the second tubular support 3 defines a rack 9 at the distal portion for locking the fins 4 and 6 in position once a flap of a heart valve has been catched. The cap 2 open like an umbrella has an elastic stop finger 10 that protrudes inside the cavity, and together with the rack 9 forms a snap-lock device. The elastic finger 10 is configured to engage at least one tooth of the rack 9 by sliding longitudinally above it when the distal portion of the second tubular support 3 is pushed into the cavity. As can be seen more clearly in the detail view of FIG. 14, the elastic finger 10 abuts against a tooth of the rack 9 and prevents the distal portion of the second tubular support 3 from accidentally exiting the cavity.

Preferably, the rack 9 will have a plurality of teeth, as illustrated in the figure, so as to allow a fine adjustment of the force with which the flaps of the valve are held. In fact, by pulling the cap 2 with gradually increasing force, the elastic finger 10 is made to slide which, step by step, will engage the teeth of the rack 9 in succession, establishing different stop positions of the cap 2. The cap 2, while advancing, tends to bring the fins 4 and 6 closer together, which thus tighten a respective flap of a valve together. By adjusting the force with which the cap 2 is pulled, the force with which the fins 4 and 6 tighten the relative valve flap as well as the angle of the fins 4 and 6 themselves are also determined. Thanks to this mechanism, the surgeon will be able to decide how strongly the valve flaps must be held, preventing fins 4 and 6 from tearing the relatively thick flaps or letting the relatively thin flaps slip out, simply by establishing how far the cap 2 should advance. Once this has been done, the elastic finger 10 abutting against a relative tooth of the rack 9 will keep the cap 2 in position.

Figure 14:
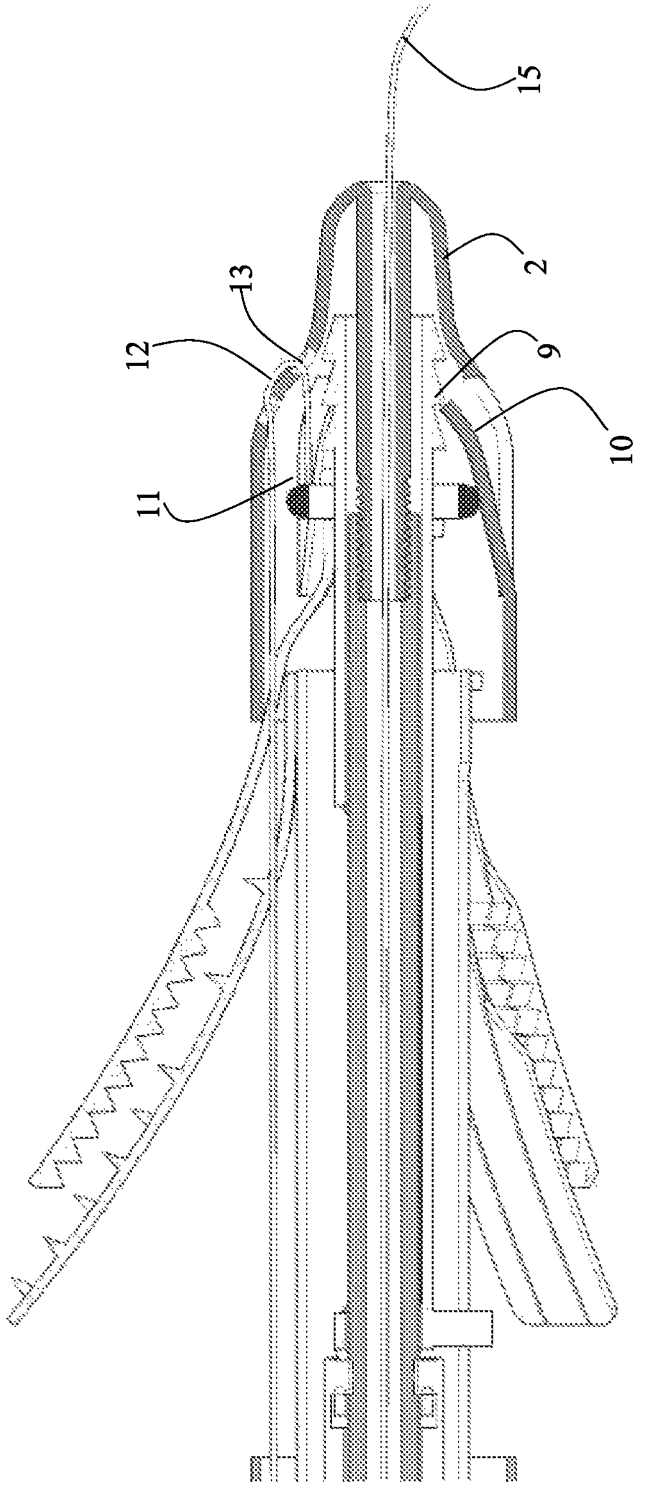
FIG. 14 is a detail view of the prosthesis in FIG. 12, shofin the elastic stop finger which engages a tooth of the first rack.
Figure 15:
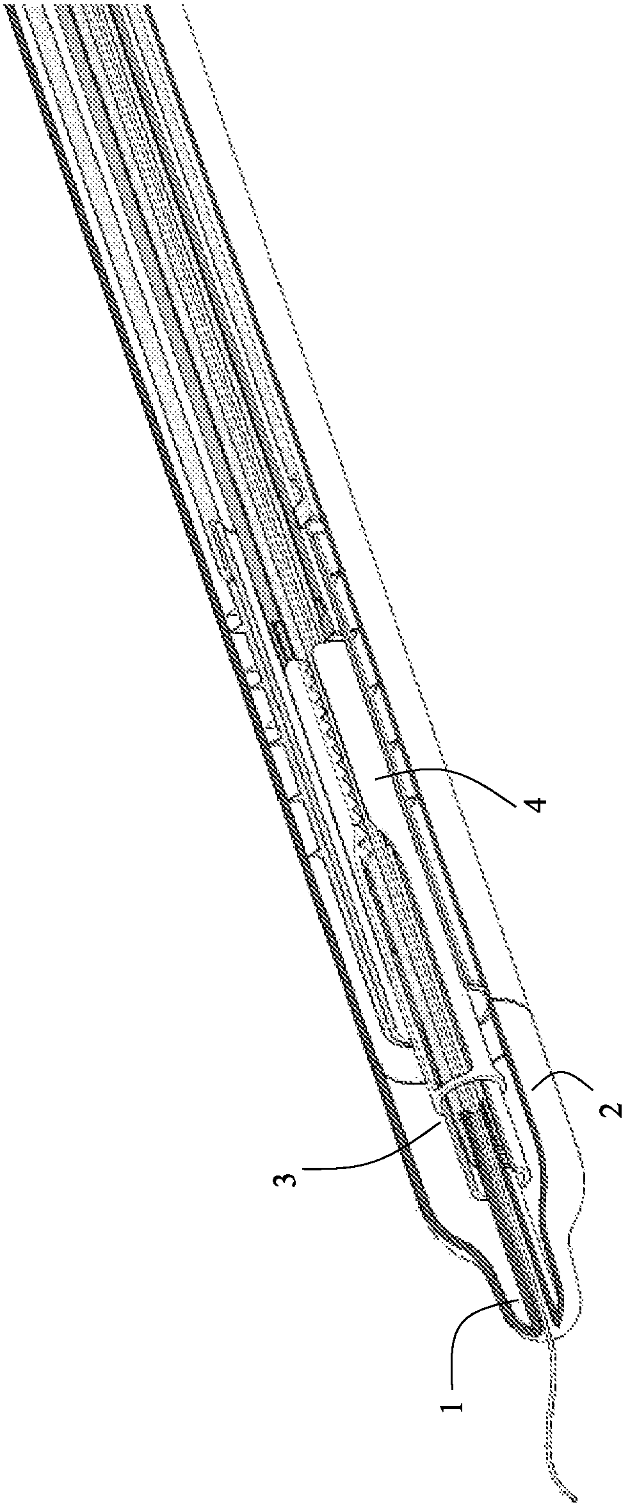
FIG. 15 shows a device according to an alternative embodiment for repairing a tricuspid or mitral valve, comprising a prosthesis of this disclosure inserted into an outermost catheter, with the fins in a retracted configuration extended longitudinally along the respective tubular support.
Figure 16:
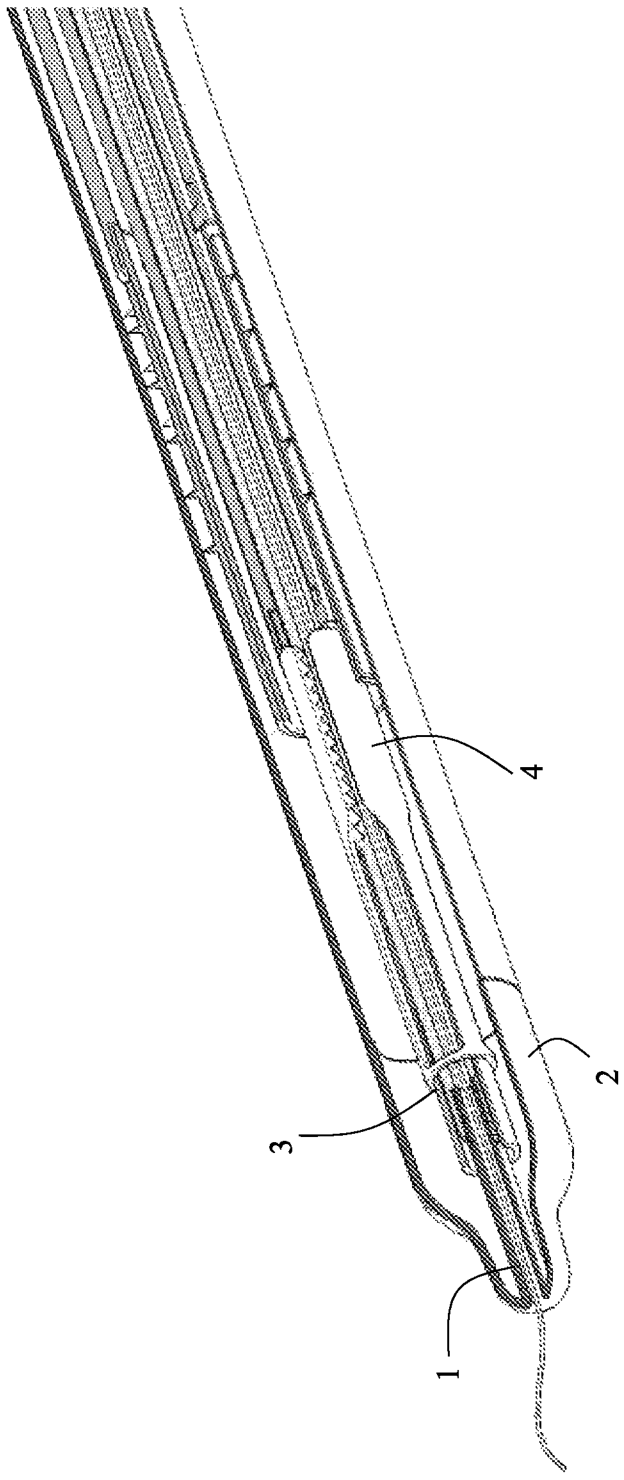
FIG. 16 shows the device of FIG. 15 while the first three fins are released.
Figure 17:
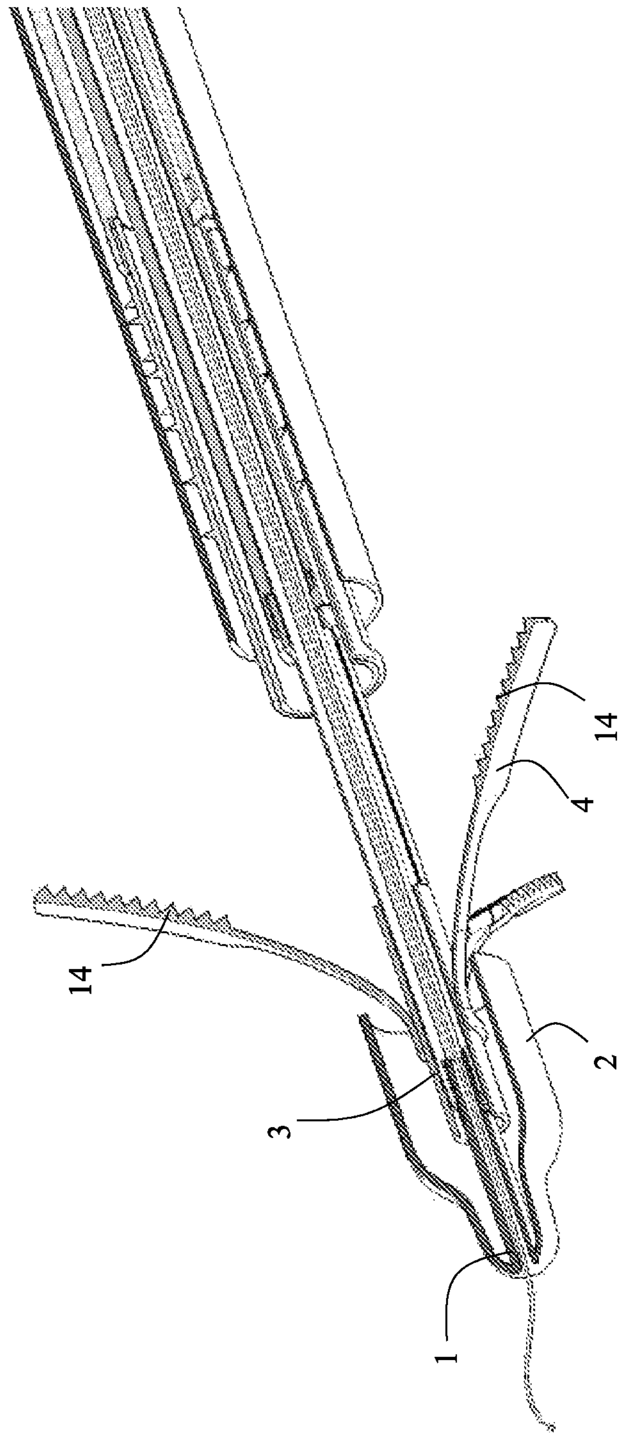
FIG. 17 shows the device of FIG. 16 with the first three fins deployed radially.
Figure 18:
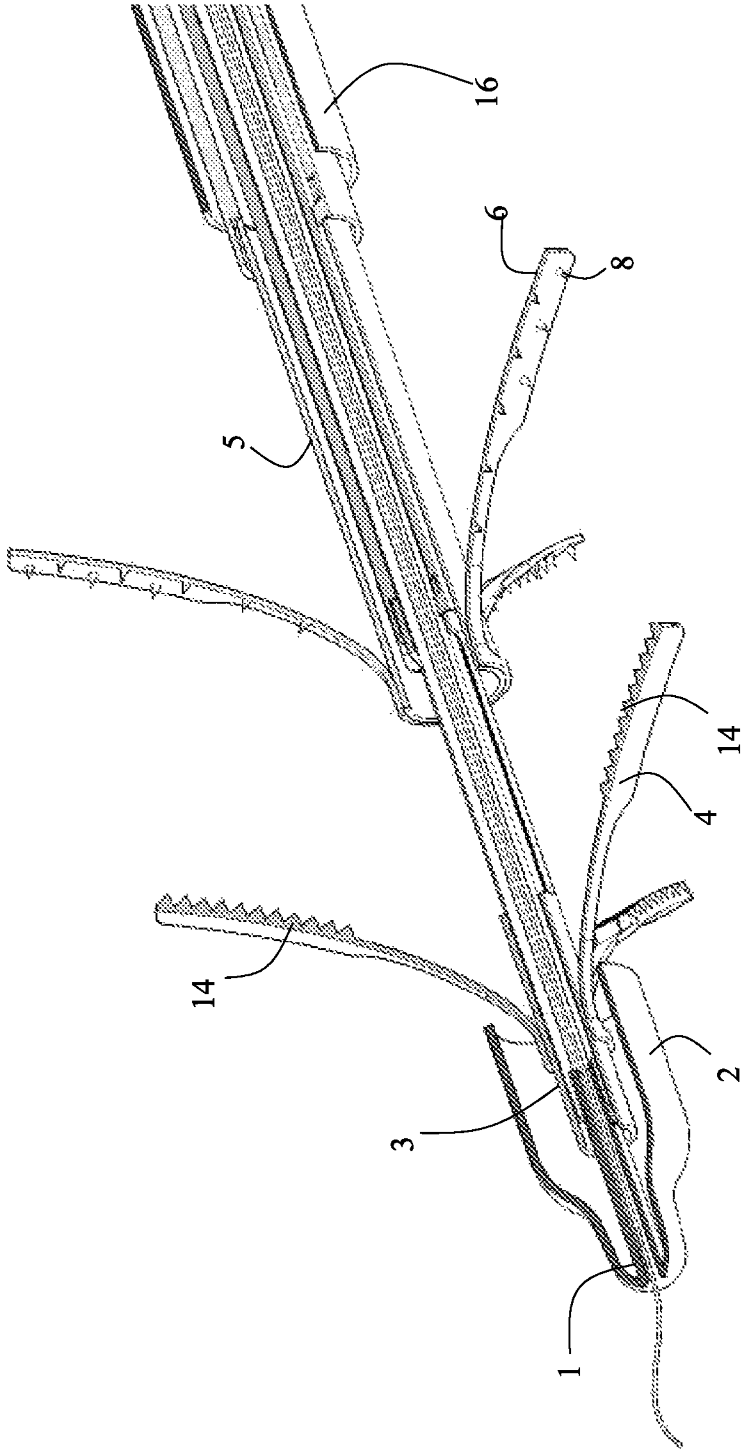
FIG. 18 shows the device of FIG. 17 with the second three fins deployed radially.
Figure 19:
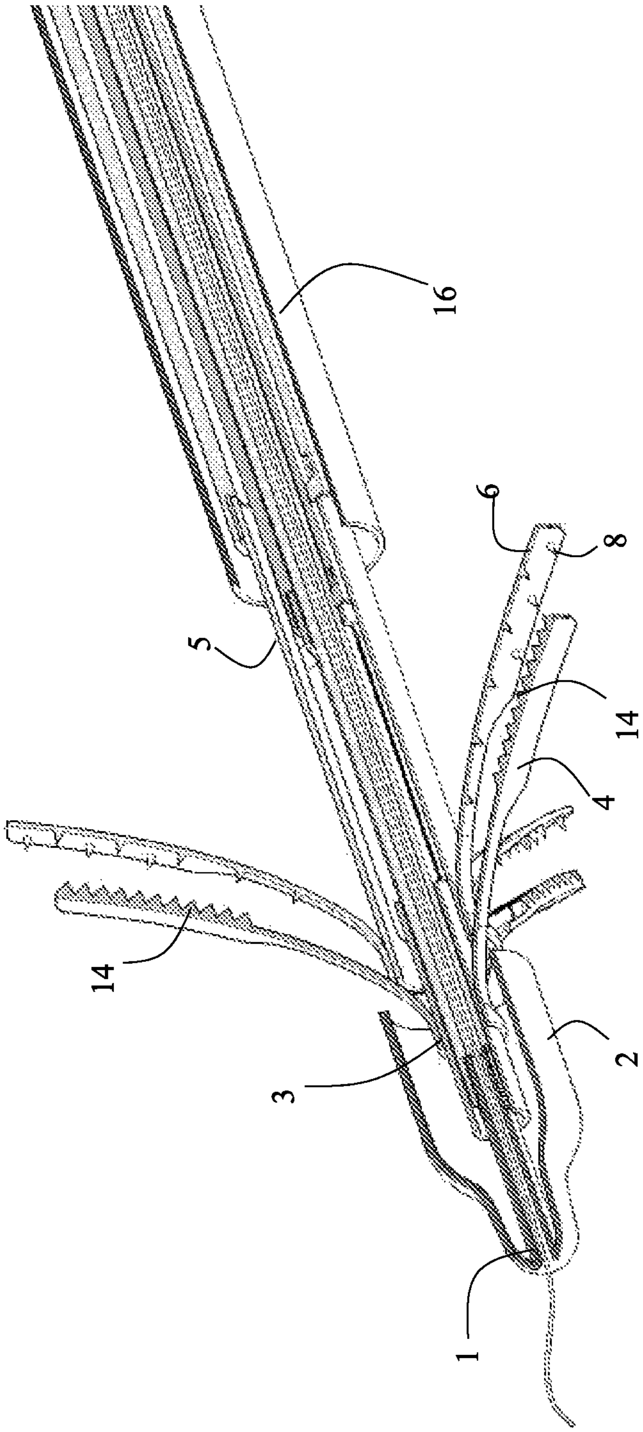
FIG. 19 shows the device of FIG. 18 when the second three fins are pushed towards the first three fins.
Figure 20:
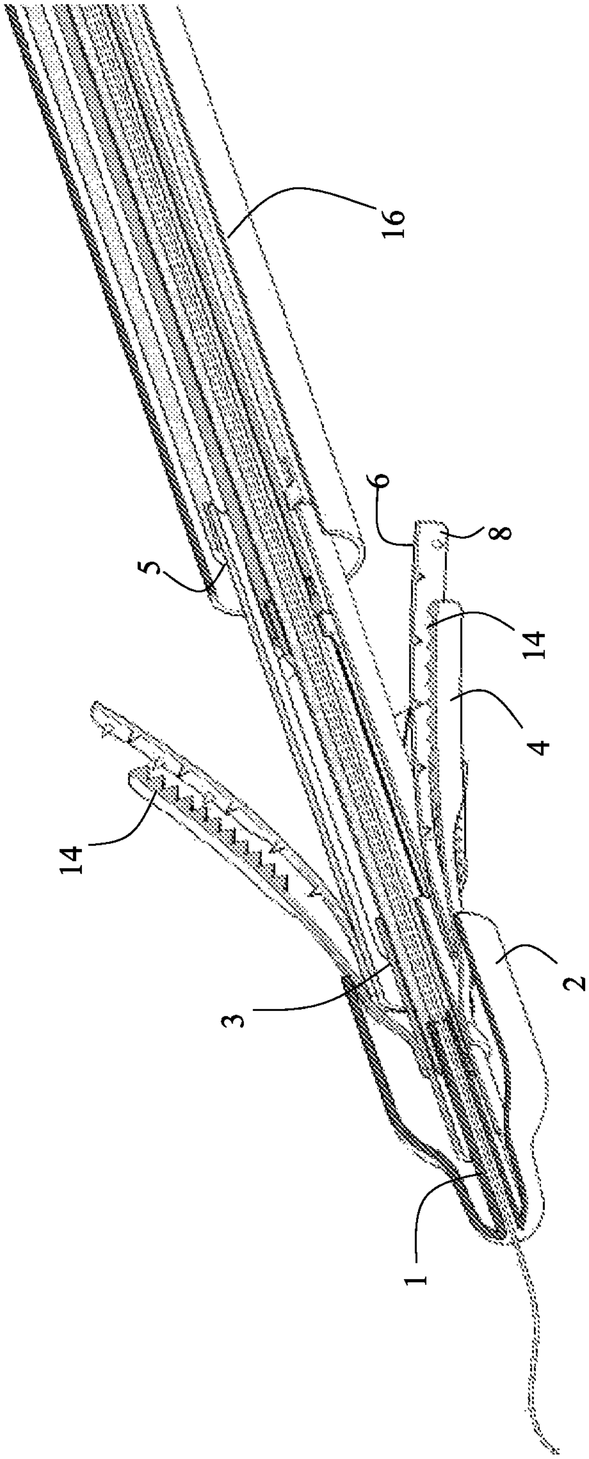
FIG. 20 shows the device of FIG. 19 with the first three fins pushed into the open cavity defined under the cap so that the first three fins are wedged and firmly locked between the cap and the third tubular support.

Pushing the distal portion of the second tubular support 3 into the cavity defined by the cap 2 could require considerable effort. To circumvent this drawback, according to an optional aspect of the prosthesis of the present disclosure, the cap 2 is screwed onto the first tubular support 1, as shown in the figures. Thanks to this expedient, it is sufficient to rotate the first tubular support 1 so as to pull the cap 2 towards the second tubular support 3, until the elastic finger 10 abuts on a respective tooth of the rack 9, blocking the second tubular support 3 in that position (FIG. 14).

According to one aspect, the cap 2 may be made of rigid material. According to an alternative aspect, the cap 2 may be made of an elastic material so as to make the thrust of the second tubular support 3 into the cavity defined by the cap 2 more gradual.

According to an aspect not shown in the drawings, the free edge of the cap 2 is shaped in such a way as to define fins that branch off from it like petals of a corolla.

When placing the prosthesis, it may be necessary to re-space the fins 4 and 6 to better catch the flaps of a heart valve, because perhaps a flap has slipped while locking the second tubular support 3 in the cavity of the cap 2. For this reason, according to an optional aspect, the prosthesis of this disclosure also has a release ring 11 positioned around the second tubular support 3 so as to slide over it, as well as a release wire 12 fixed to the release ring 11, which passes through at least one through hole 13 in the cap 2 and runs longitudinally along the outer wall of the third tubular support 5. The release wire 12 and the release ring 12 are configured so that, by pulling the release wire 12 in the manner shown in FIG. 13, the release ring 11 moves longitudinally entering the cavity defined by the cap 2 by lifting the elastic finger 10. Consequently, the elastic finger 10 of the engagement will no longer abut against a tooth of the rack 9 and will allow the distal portion of the second tubular support 3 to come out of the cavity. The fins 4 and 6 may then be repositioned to better catch the flaps of a heart valve, after which they will be stopped in that configuration by pushing them longitudinally towards the cavity defined by the cap 2 until the elastic stop finger 10 engages a tooth of the rack 9.

According to an optional aspect, a surgical guide wire 15 is inserted into the longitudinal axial hole of the first tubular support 1, so as to be able to guide the prosthesis in the center of the heart valve.

Figure 10:
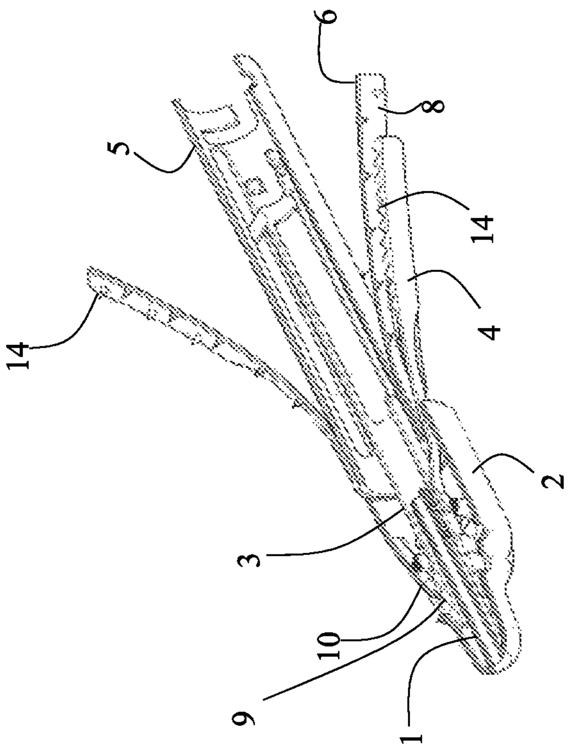
FIG. 10 shows the prosthesis of the device of FIG. 9, after having released a first, a second and a third catheter from the respective tubular supports and after having removed a fourth outermost catheter.
Figure 11:
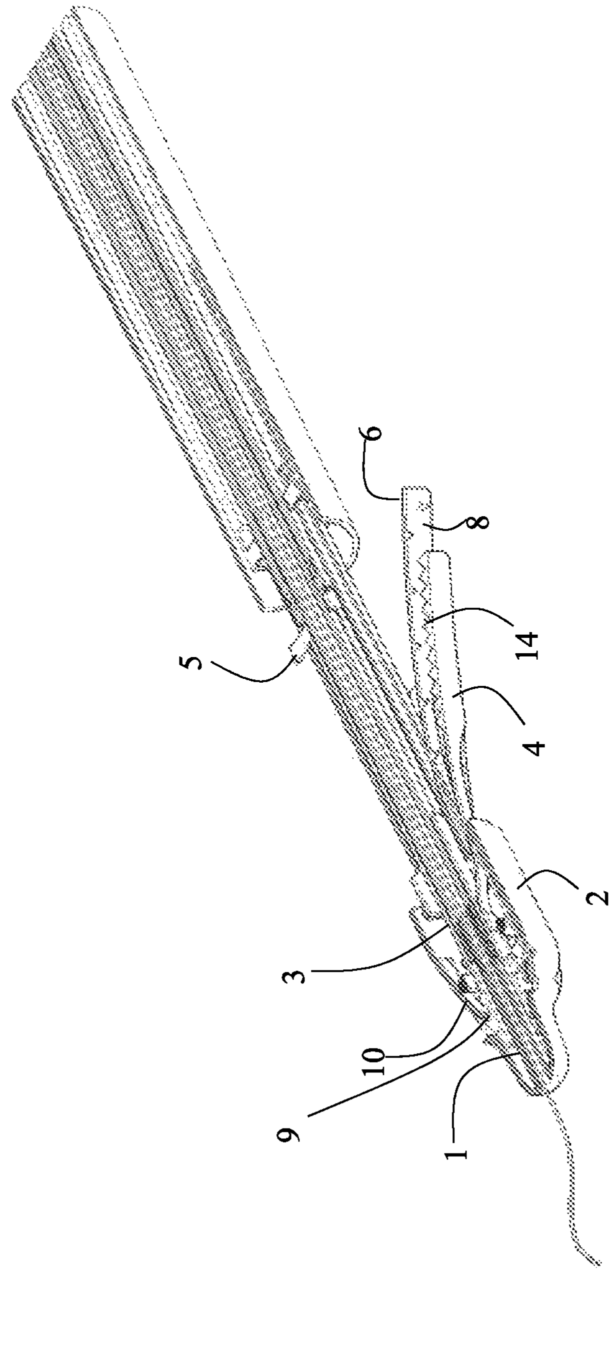
FIG. 11 shows the prosthesis of FIG. 10 tied to the respective first, second and third catheters, with the elastic stop finger which does not engage a tooth of a first rack of the snap lock.
Figure 12:
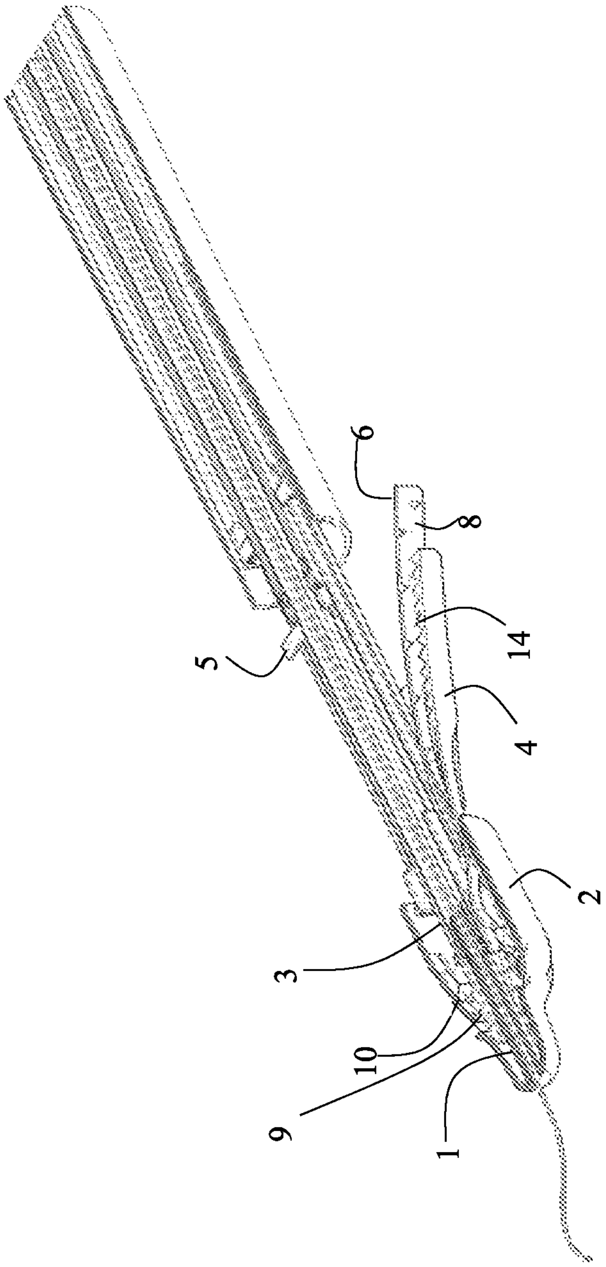
FIG. 12 shows the prosthesis of FIG. 11 tied to the respective first, second and third catheters to allow the repositioning of the fins, with the elastic stop finger which engages a tooth of the first rack of the snap lock on the second tubular support.

In order to place the prosthesis of this disclosure, shown in FIG. 10, the device of this disclosure comprises a first catheter, a second catheter and a third catheter releasably connected to the first tubular support 1, the second tubular support 3 and the third tubular support 5, respectively. Through the second and third catheters it is possible to move longitudinally and rotate the fins 4 and 6, while with the first catheter it is possible to pull the cap 2 towards the fins 4 and 6. Once the fins 4 and 6 tighten the flaps of a heart valve and the elastic finger 10 engages a tooth of the rack 9, the first, second and third catheters are released and the prosthesis (FIG. 10) is left in the patient's body.

According to an aspect not shown in the drawings, the first tubular support 1, the second tubular support 3 and the third tubular support 5 are integral with the corresponding catheters, respectively the first catheter, the second catheter and the third catheter, and constitute an extension thereof. Once the prosthesis is correctly installed in the patient's body, the tubular supports are separated from their respective catheters by a cutting operation. In this way, the length of the tubular supports that are left in the patient's body is determined by the surgeon as needed by establishing the point in which to cut the respective catheters.

Figure 21:
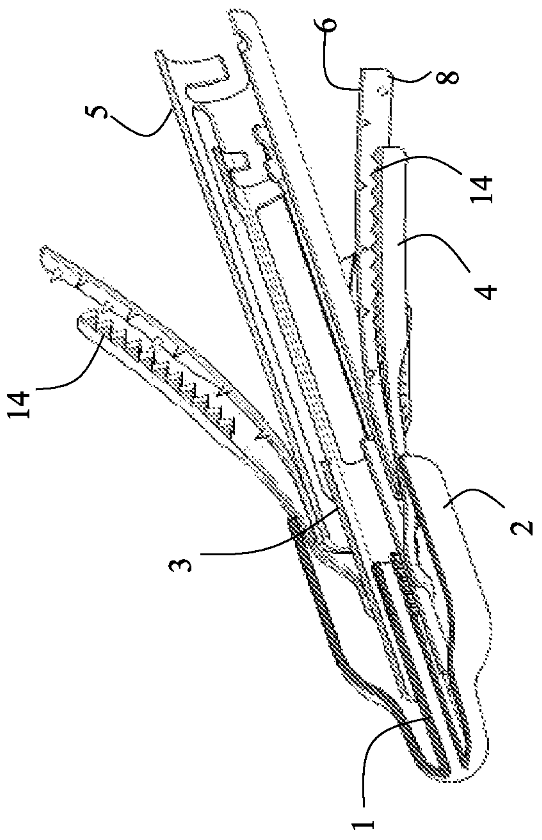
FIG. 21 shows the prosthesis of the device of FIG. 20, after having released a first, a second and a third catheter from the respective tubular supports and after having removed a fourth outermost catheter.

An alternative embodiment of a prosthesis according to this disclosure is illustrated in FIGS. 15 to 24, in which the elements corresponding to those illustrated in FIGS. 4 to 14 are designated with the same numerical references. FIGS. 15 to 20 are similar to FIGS. 4 to 9 and show how the fins 4 and 6 unfold and tighten so as to pinch the flaps of a heart valve, and FIG. 21 is similar to FIG. 10 and shows the prosthesis which is implanted in the patient's body. The prosthesis according to this alternative embodiment has a longitudinal sliding stop device illustrated in FIGS. 22 to 24. As for the embodiment shown in FIGS. 13 and 14, the outer wall of the second tubular support 3 defines in correspondence of its distal portion a first rack 9 intended, as in FIGS. 13 and 14, to engage corresponding mechanical stop defined on the cap 2.

Figure 13:
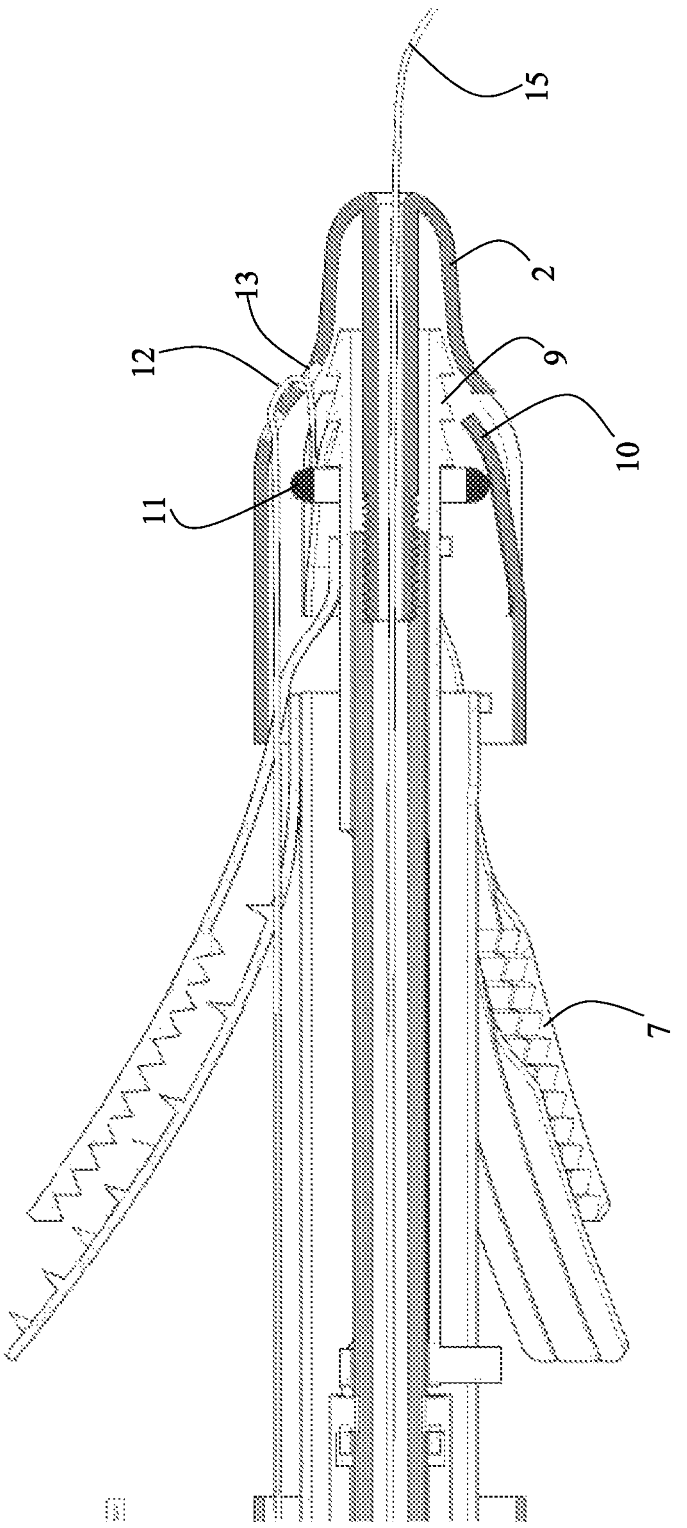
FIG. 13 is a detail view of the prosthesis in FIG. 11, shofin the elastic stop finger raised from the first rack through the release ring.
Figure 22:
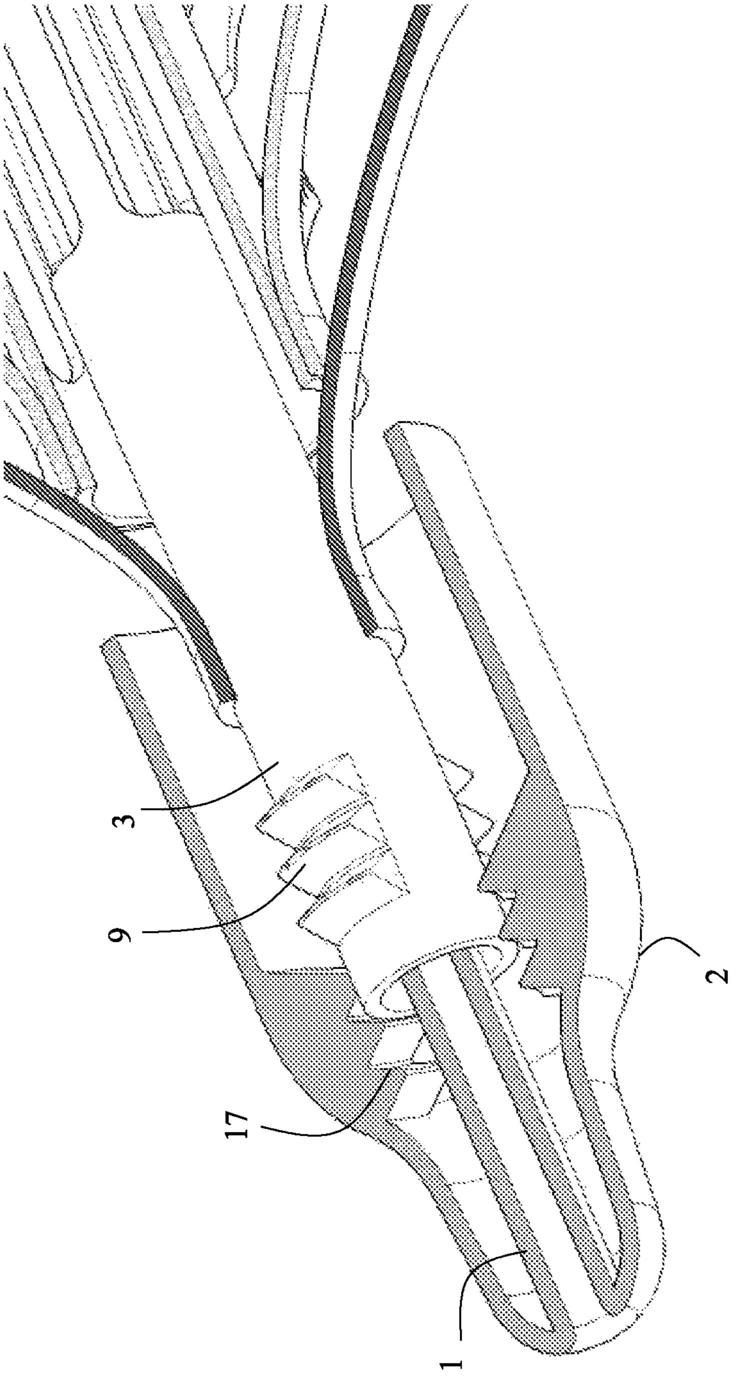
FIGS. 22 to 24 show in sequence how to hook the second tubular support 3 to the cap by engaging the first rack with the second rack defined on an internal wall of the cap.
Figure 23:
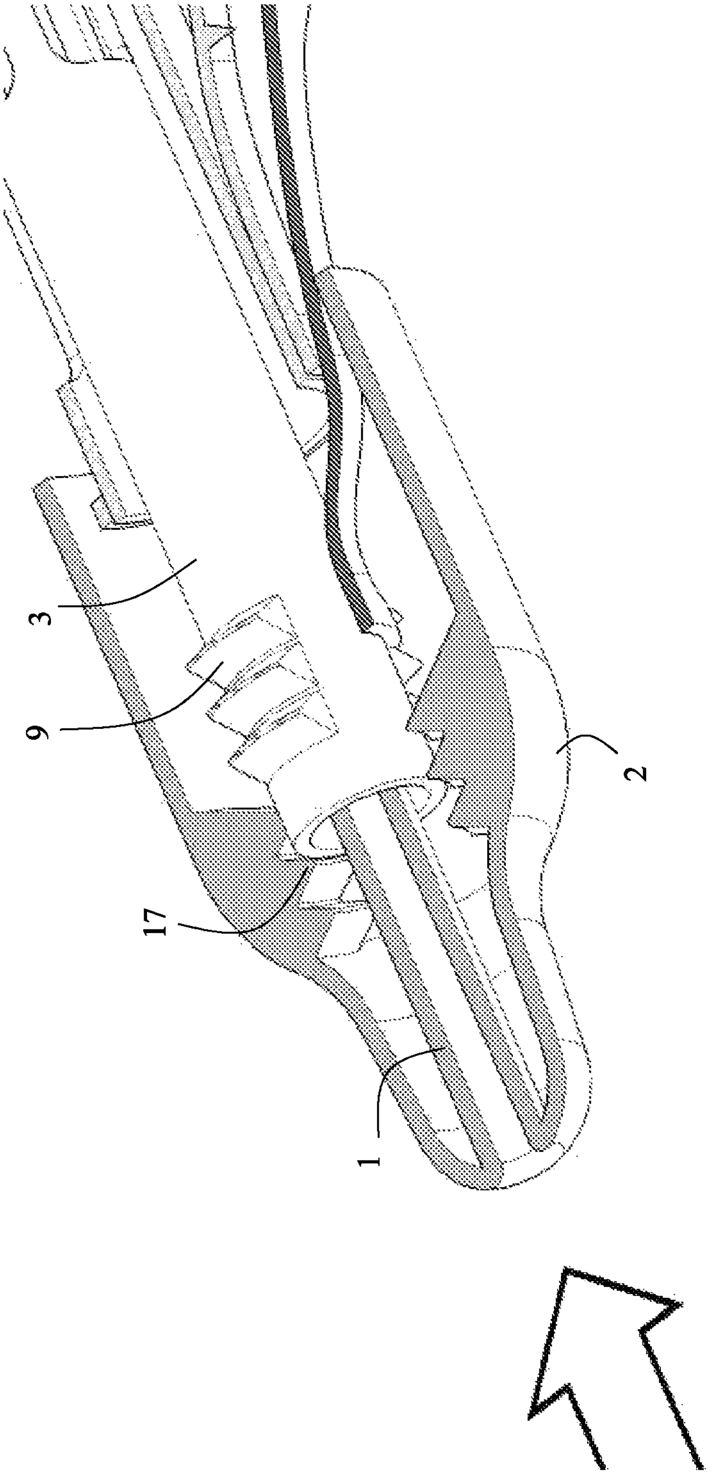
Figure 24:
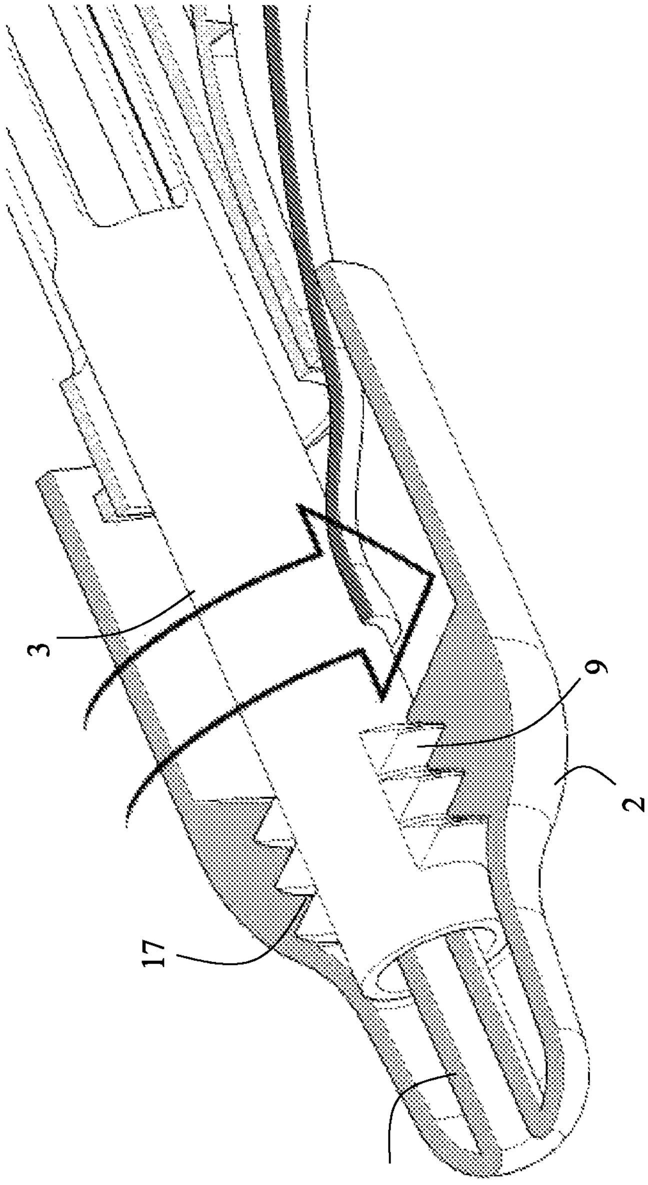

Unlike FIGS. 13 and 14, in which the mechanical stop are substantially constituted by an elastic finger 10, in the embodiment of FIGS. 22 to 24 the mechanical stop comprise a second rack 17 defined on an internal face of the cap 2 and configured to engage the first rack 9. As shown in the sectional views of FIGS. 22 and 23, the second tubular support is pushed so that the cap 2 tightens the fins 4 and 6 against each other by sliding longitudinally the first rack 9 inside the cap 2. Once the cap 2 has been positioned so as to tighten the fins 4 and 6 with the desired force, the second tubular support 3 is rotated so that the teeth of the first rack 9 engage respective teeth of the second rack 17 inside the cap 2, as shown in FIG. 24, preventing the second tubular support 3 from accidentally slipping off.

If it is necessary to reposition the prosthesis, for example because the heart valve flaps have not been properly catched, the second tubular support 3 is rotated so as to free the first rack 9 from the second rack 17, then the second tubular support 3 is slid so as to free the fins 4 and 6 which, once repositioned, can be locked in the manner indicated above. As for the embodiment of FIGS. 4 to 14, once the fins 4 and 6 tighten the flaps of a heart valve and the first rack 9 is locked, this time thanks to respective teeth of the second rack 17, all the first, second and third catheters are released and the prosthesis (FIG. 21) is left in the patient's body.

An outermost catheter 16, configured to slide longitudinally over the outer wall of the third tubular support 5, keeps the fins of the second plurality of fins 6 in the respective retracted configuration. Optionally, the fourth catheter 16 is configured to abut against a free edge of the cap 2.

Figure 3:
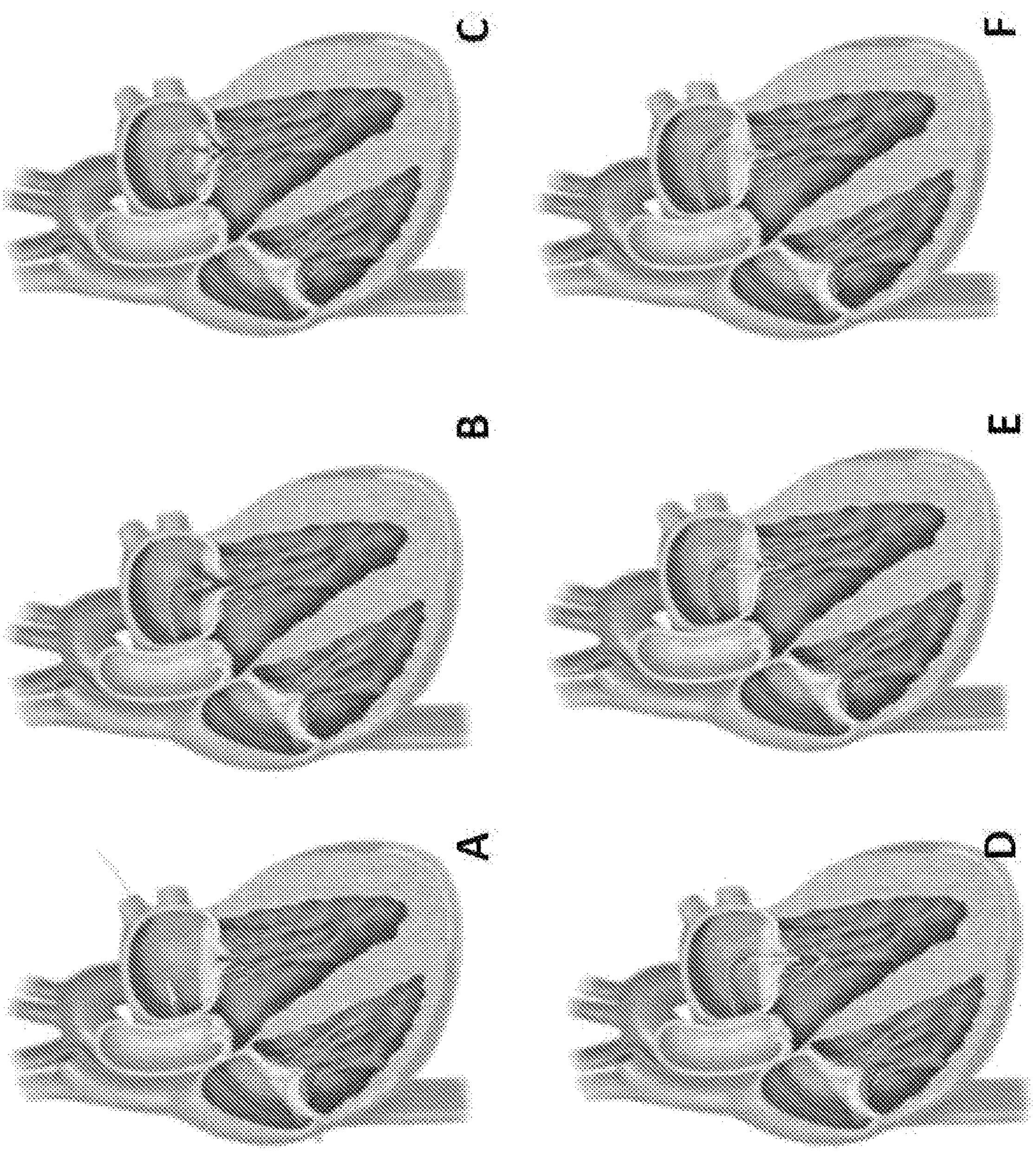
FIG. 3 shows various steps for implanting the so-called MITRACLIP™ catching device to the flaps of a heart valve.
Figure 4:
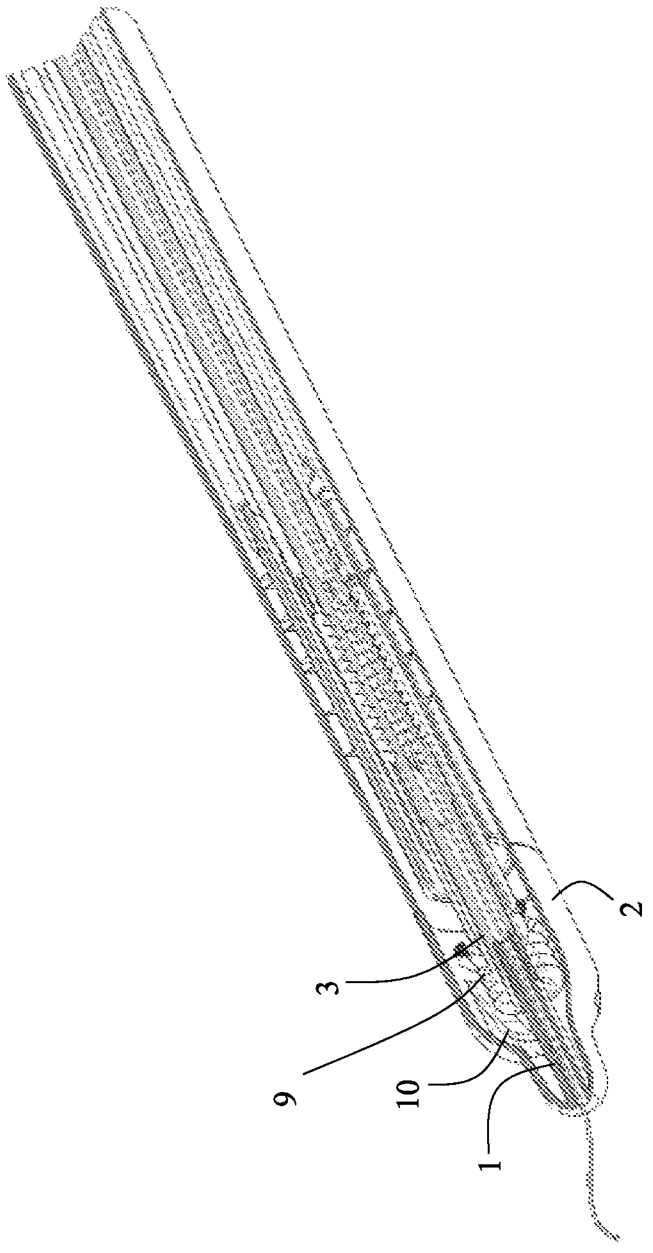
FIG. 4 shows a device according to an embodiment for repairing a tricuspid or mitral valve, comprising a prosthesis of this disclosure inserted into an outermost catheter, with the fins in a retracted configuration extended longitudinally along the respective tubular support.
Figure 5:
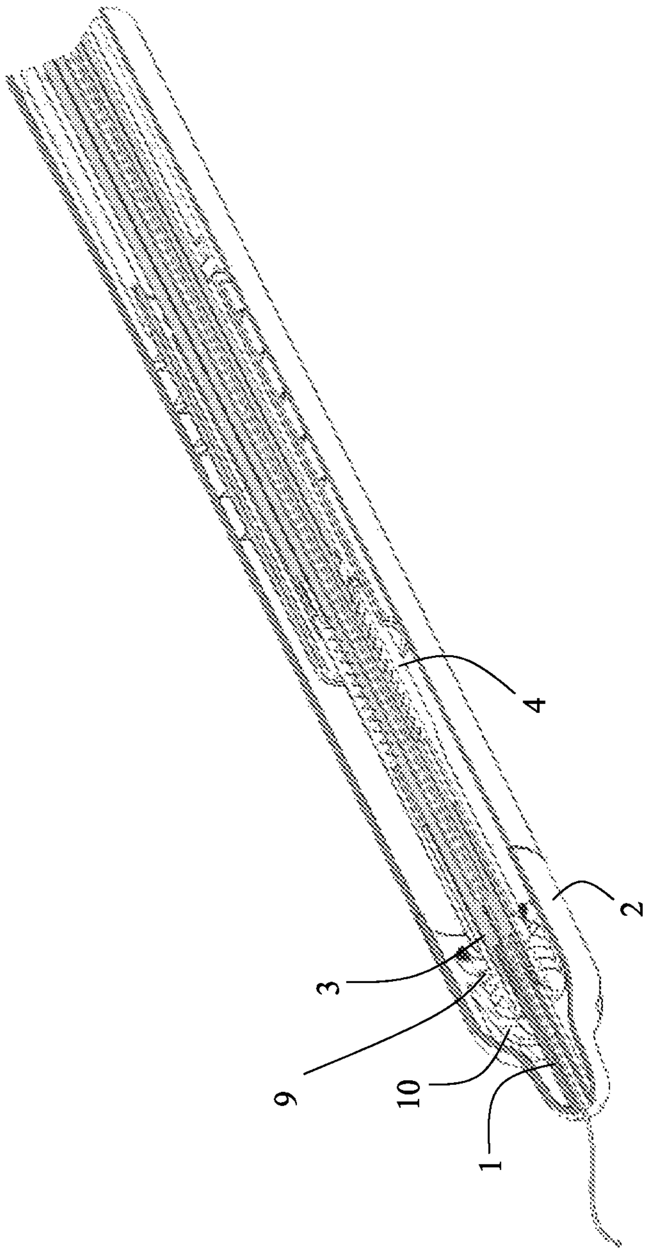
FIG. 5 shows the device of FIG. 4 while the first three fins are released.
Figure 6:
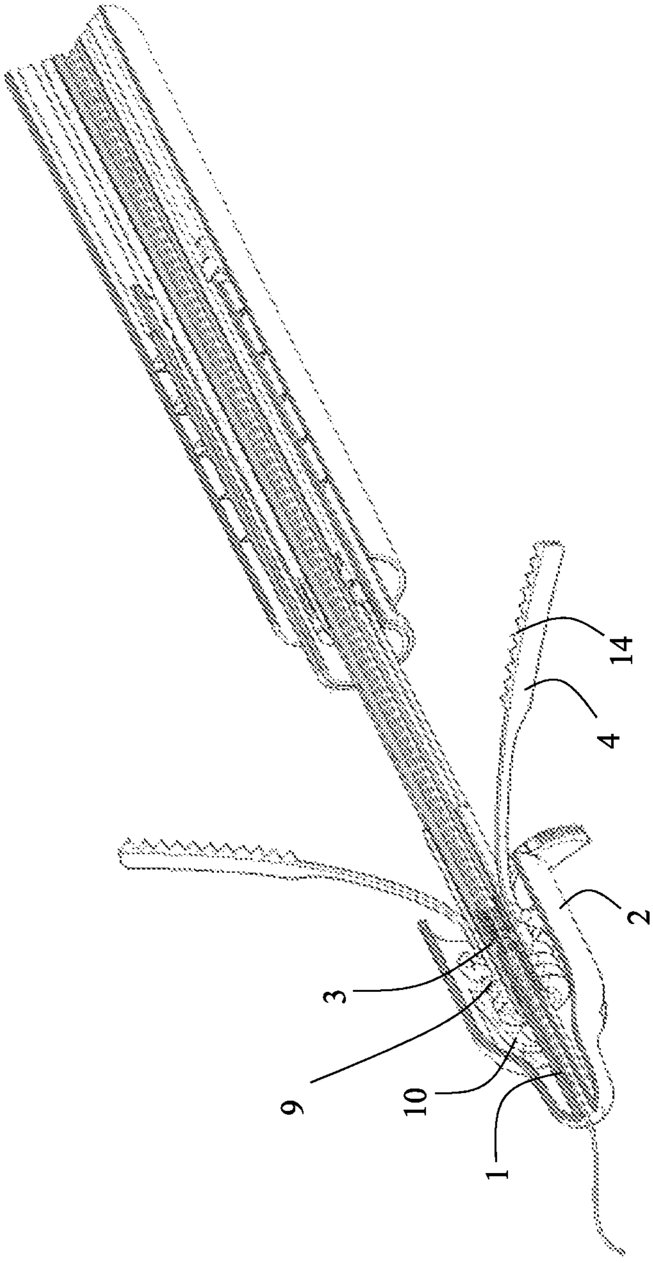
FIG. 6 shows the device of FIG. 5 with the first three fins deployed radially.
Figure 7:
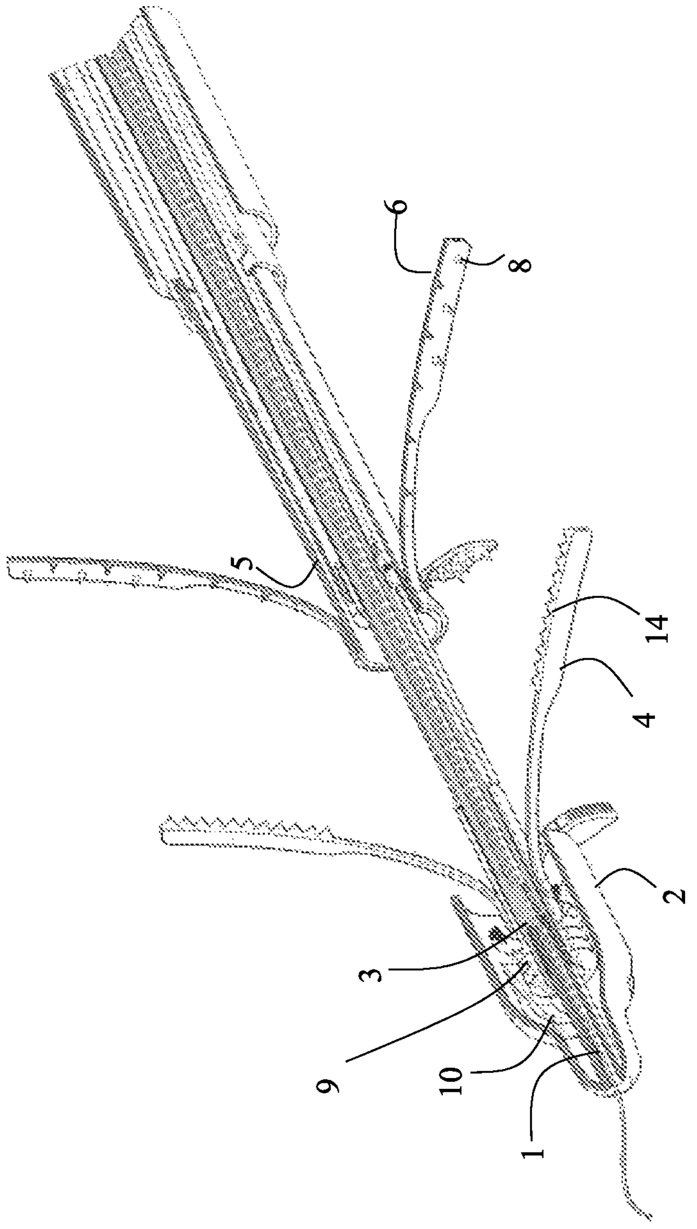
FIG. 7 shows the device of FIG. 6 with the second three fins deployed radially.
Figure 8:
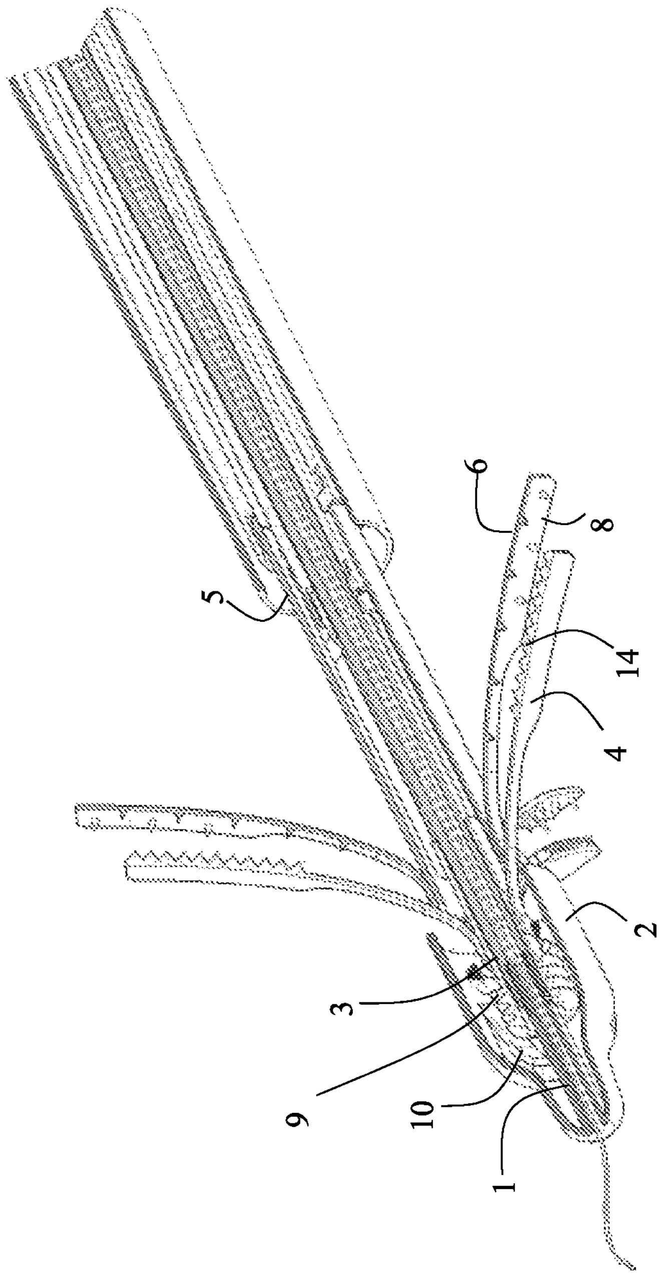
FIG. 8 shows the device of FIG. 7 when the second three fins are pushed towards the first three fins.
Figure 9:
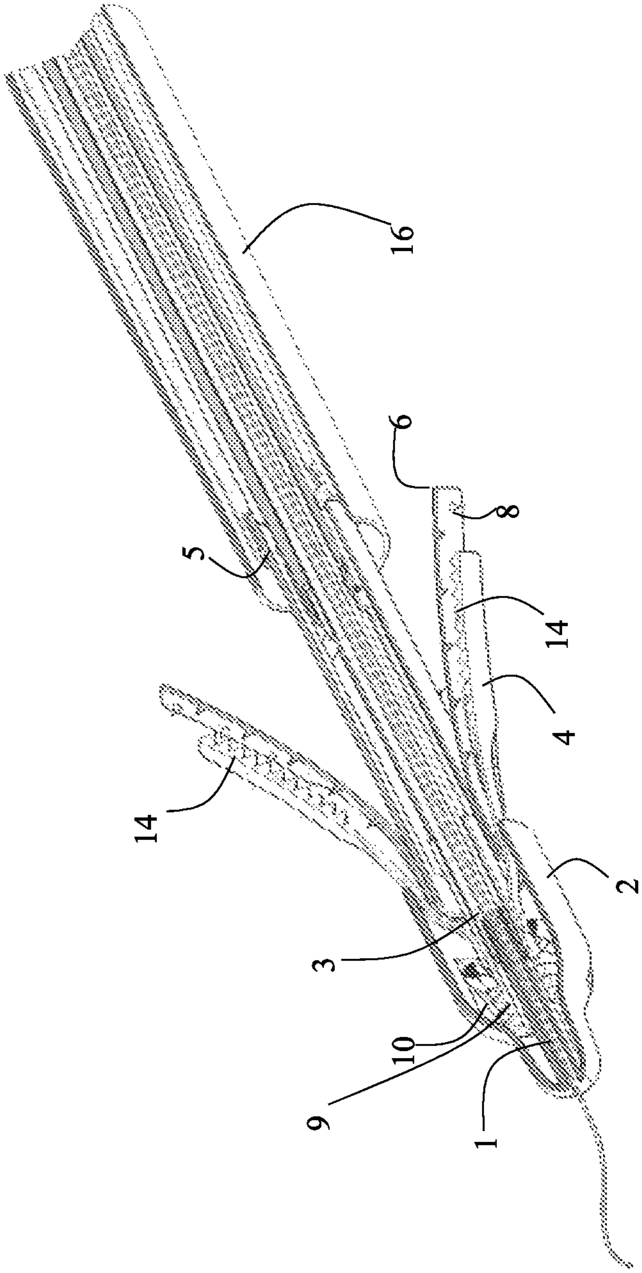
FIG. 9 shows the device of FIG. 8 with the first three fins pushed into the open cavity defined under the cap so that the first three fins are wedged and firmly locked between the cap and the third tubular support.

The outermost catheter 16 is adapted to be inserted into a patient's heart through a vein, as shown in FIG. 3 and commonly done for the well-known MITRACLIP™ device, or through an incision in the patient's chest.

The prosthesis will be made of biocompatible materials suitable for heart prostheses to be implanted in the patient's heart.

The invention claimed is:

1. A prosthesis for a tricuspid or mitral valve, comprising:

a first tubular support having a first tubular body with a respective longitudinal axial hole, terminating at a distal end with a cap open like an umbrella around said first tubular support, wherein a cavity open on one side is defined between said cap open like an umbrella and an outer wall of said first tubular support;

a second tubular support having a second tubular body with a respective longitudinal axial hole, said second tubular body being configured to slide in a longitudinally guided manner over an external wall of and concentrically to said first tubular body of the first tubular support, having at least a first plurality of fins constrained to a distal portion of the second tubular body of the second tubular support, the fins of said first plurality of fins being configured to pass autonomously from a respective retracted configuration, in which they are extended longitudinally along an external wall of said second tubular body of the second tubular support, to a respective open configuration, in which they are open radially away from the external wall of the second tubular body of the second tubular support, as soon as they are free to unfold;

a third tubular support having a third tubular body with a respective longitudinal axial hole, configured to slide in a longitudinally guided manner above and concentrically to said second tubular body of the second tubular support and above said first plurality of fins in the respective retracted configuration, having at least a second plurality of fins tied to a distal portion of the third tubular support, the fins of said second plurality of fins being configured to pass autonomously from a respective retracted configuration, in which they are extended longitudinally along an external wall of said third tubular support, to a respective open configuration, in which they are open radially away from the external wall of the third tubular support, as soon as they are free to unfold;

wherein the fins of said first plurality of fins and of said second plurality of fins have respective facing surfaces configured to cooperate with each other to catch a flap of a tricuspid or mitral valve by squeezing it from opposite faces;

the outer wall of said second tubular support defines, in correspondence with said distal portion, a first rack of a locking device with longitudinal sliding stop;

said cap open like an umbrella having a mechanical stop, configured to prevent longitudinal sliding of the second tubular support when said mechanical stop engage said first rack.

2. The prosthesis according to claim 1, wherein said locking device with longitudinal sliding stop is a snap lock and said umbrella-like open cap, having said mechanical stop, has an elastic stop finger, which protrudes inside said cavity and is configured to engage at least one tooth of said first rack by sliding above it when the distal portion of the second tubular support is pushed into said cavity by sliding above said first tubular support, so as to prevent the distal portion of the second tubular support from accidentally coming out of said cavity.

3. The prosthesis of claim 2, comprising:

an release ring positioned around said second tubular support so as to slide over it;

a release wire fixed to the release ring, which passes through at least one through hole in the cap and runs longitudinally along said external wall of the third tubular support;

said release wire and said release ring being configured so that, by pulling the release wire, the release ring moves longitudinally entering the cavity defined by the cap and lifting the elastic stop finger from said first rack allowing the distal portion of the second tubular support to exit from said cavity.

4. The prosthesis according to claim 1, wherein said cap open like an umbrella, having said mechanical stop, has a second rack defined on an internal face of the cap and configured to engage the first rack by axially rotating said second tubular support axially on itself with respect to said cap.

5. The prosthesis according to claim 1, in which said cap is screwed onto said first tubular support.

6. The prosthesis according to claim 1, in which said first fins and said second fins are made of Nitinol and are configured to unfold radially as soon as they are free to unfold.

7. The prosthesis according to claim 1, in which said respective facing surfaces of said fins have teeth and/or harpoons for catching flaps of a tricuspid or mitral valve.

8. The prosthesis according to claim 1, further comprising a surgical guide wire inserted into the longitudinal axial hole of the first tubular support.

9. The prosthesis according to claim 1, wherein said first plurality of fins comprises three first fins angularly spaced by 120°, and wherein said second plurality of fins comprises three second fins angularly spaced by 120°.

10. A device for repairing a tricuspid or mitral valve, comprising:

a prosthesis according to claim 1;

a first catheter releasably connected to said first tubular support;

a second catheter releasably connected to said second tubular support;

a third catheter releasably connected to said third tubular support;

a fourth catheter, configured to slide longitudinally over the outer wall of said third tubular support and over the fins of said second plurality of fins in the respective retracted configuration.

11. The device according to claim 1, wherein said fourth catheter is configured to abut against a free edge of said cap open like an umbrella of the prosthesis.

* * * * *